United States Patent [19]

Sakai et al.

[11] Patent Number: 4,966,038
[45] Date of Patent: Oct. 30, 1990

[54] ULTRASONIC MICROSCOPE

[75] Inventors: Mitsugu Sakai, Hachioji; Koichi Karaki, Tokyo; Yasuo Sasaki, Hachioji, all of Japan

[73] Assignee: Olympus Optical Co., Ltd., Tokyo, Japan

[21] Appl. No.: 369,644

[22] Filed: Jun. 21, 1989

[30] Foreign Application Priority Data

Jul. 1, 1988 [JP] Japan .................. 63-162713

[51] Int. Cl.$^5$ .................................. G01N 29/04
[52] U.S. Cl. .......................................... 73/606
[58] Field of Search ............... 73/606, 615, 633, 618, 73/619

[56] References Cited

U.S. PATENT DOCUMENTS 4,683,751  8/1987  Imade et al. ..................... 73/606

FOREIGN PATENT DOCUMENTS 0072052   4/1983   Japan ............................. 73/606
58-196453 11/1983  Japan .
59-44582  10/1984  Japan .
0154961   6/1988   Japan ............................. 73/606

OTHER PUBLICATIONS

"Cryogenic Acoustic Microscopy", by J. Heiserman et al., J. Acoust. Soc. Am., 67(5), May 1980, pp. 1629–1637.

Primary Examiner—Hezron E. Williams
Assistant Examiner—Louis M. Arana
Attorney, Agent, or Firm—Frishauf, Holtz, Goodman & Woodward

[57] ABSTRACT

An ultrasonic microscope comprises an acoustic lens, a supporting rod for supporting a sample, a supporting plate for supporting the lens and a drive mechanism for two-dimensionally shifting the lens supporting plate, thereby setting a scanning region, and driving the lens supporting plate to scan the sample to obtain an ultrasonic image thereof. The drive mechanism includes magnetic coils and permanent magnets for shifting the supporting plate by generating a magnetic field, a first power source for producing an electric current for designating the scanning region, a second power source for producing an electric current for scanning, and an adder for adding the electric currents from the first and second power sources and delivering the resulting current to the magnetic coils.

8 Claims, 7 Drawing Sheets

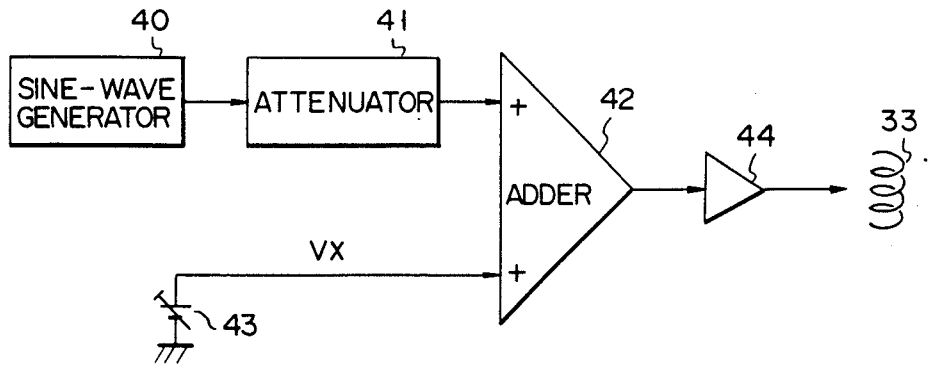
F I G. 3A
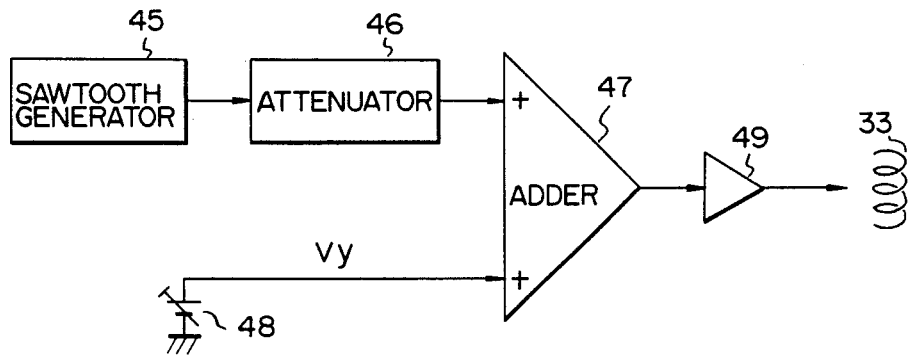
F I G. 3B

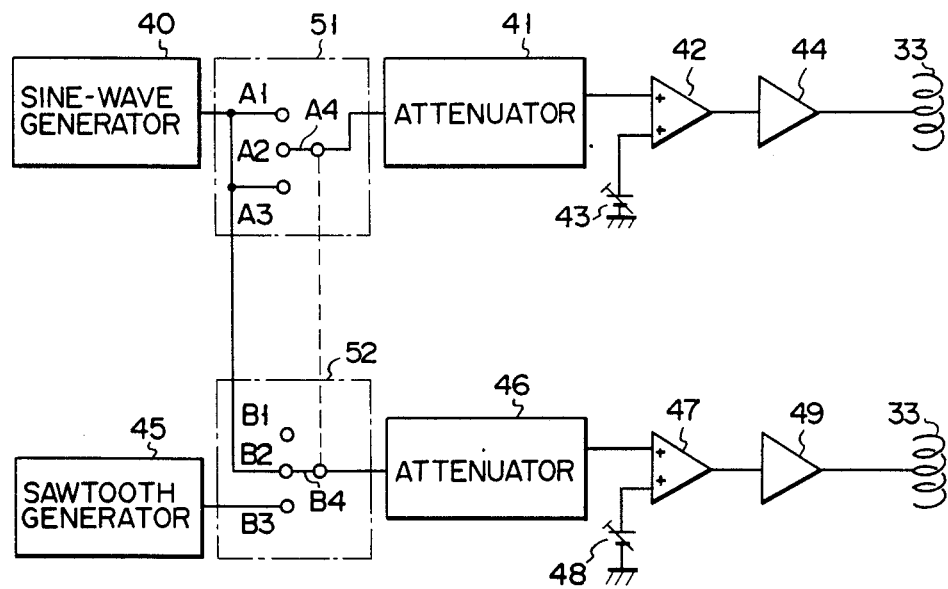
F I G. 4

ULTRASONIC MICROSCOPE

BACKGROUND OF THE INVENTION

1. Field of the Invention

The present invention relates to an ultrasonic microscope.

2. Description of the Related Art

Conventionally disclosed in Japanese Patent Publication No. 59-44582 and Japanese Patent Disclosure No. 58-196453, for example, are ultrasonic microscopes in which a sample to be observed is two-dimensionally scanned with an ultrasonic beam, and the resulting transmitted or reflected waves are received to obtain an ultrasonic image of the sample.

Also, a cryogenic ultrasonic microscope capable of providing a high-resolution ultrasonic image is described in The Journal of Acoustic Society of America, vol. 67 (1980), pp. 1,629 to 1,637. In this microscope, a cryogenic fluid, such as liquid nitrogen, liquid argon, or liquid helium, which is lower in sound transmission speed and acoustic absorptivity than water, is used as an ultrasonic transmission medium interposed between an acoustic lens and a sample.

These conventional microscopes, however, are complicated in construction, and cannot enjoy a wide scanning range without lowering their operating efficiency.

SUMMARY OF THE INVENTION

The object of the present invention is to provide an ultrasonic microscope of a simple construction, capable of automatically selecting a desired field of view with high accuracy and reproducibility.

BRIEF DESCRIPTION OF THE DRAWINGS

FIGS. 3A and 3B are diagrams showing driver circuits for driving the acoustic lens in the x- and y-directions, respectively;

FIG. 4 is a diagram showing a modification of the driver circuit arrangement;

DETAILED DESCRIPTION OF THE PREFERRED EMBODIMENTS

Figure 1:
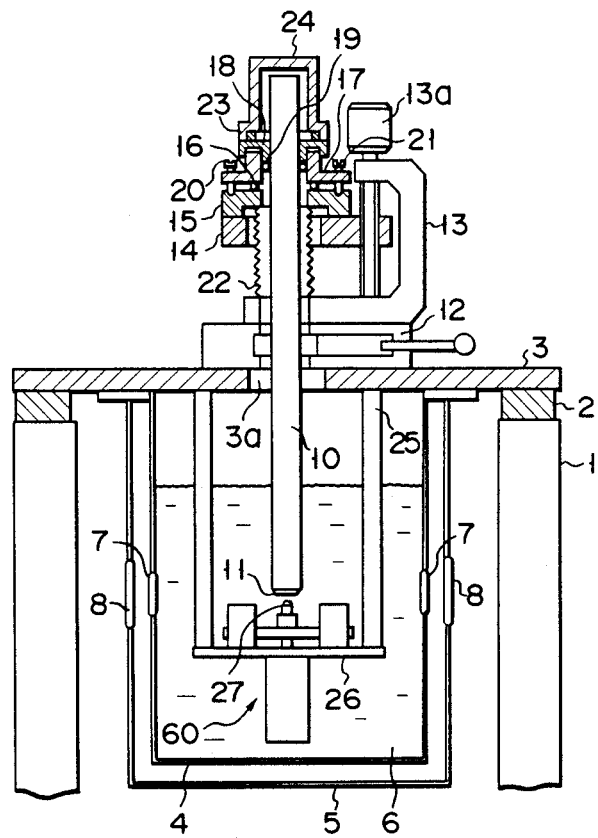
FIG. 1 is a schematic view showing an outline of an ultrasonic microscope according to an embodiment of the present invention.

FIG. 1 shows a cryogenic ultrasonic microscope according to an embodiment of the present invention. In FIG. 1, base plate 3 is horizontally mounted on microscope body 1 with the aid of air damper 2. Adiabatic vessel 4 is hermetically attached to the lower surface of plate 3, and cover 5 is disposed outside the vessel at a predetermined distance therefrom. Vessel 4 contains liquid nitrogen 6 as an ultrasonic transmission medium, and a vacuum is formed between vessel 4 and cover 5, in order to prevent a temperature rise. Vessel 4 and cover 5 have windows 7 and 8, respectively, each formed of a transparent plate through which the inside of the vessel can be observed.

Base plate 3 has central opening 3a, through which sample rod 10, formed of a stainless-steel pipe, is vertically moved or tilted so that its lower end portion can be immersed in liquid nitrogen 6 in adiabatic vessel 4. Rod 10 bears sample 11 on its lower end face. Gate valve 12 is disposed on plate 3 so that rod 10 penetrates the valve. When sample rod 10 is removed for sample replacement, valve 12 is closed to seal vessel 4. Micrometer head 13 is disposed on gate valve 12 so that rod 10 penetrates the head. Movable plate 14 can be moved vertically or in the z-direction by rotating micrometer 13a of head 13.

Movable plate 14 is threadedly engaged with micrometer 13a so that sample rod 10 penetrates plate 14. Stationary block 15 is disposed on plate 14 so that the upper portion of rod 10 penetrates block 15. Movable block 17 is provided over block 15 with O-ring 16 between the two blocks. Sleeve 18 is located in engagement with movable block 17 so that sample rod 10 is supported by the inner peripheral surface of the sleeve. O-ring 19 is interposed between block 17 and rod 10. A pair of adjust screws 20 and 21 for each of the x- and y-directions (only those for the x-direction are shown in FIG. 1) vertically penetrate movable block 17 so that sample rod 10 is situated between the screws. Screws 20 and 21 are used to adjust the tilt of sample 11 with respect to the x- and y-directions which intersect at right angles within a horizontal plane. By rotating these screws, the tilt of movable block 17, with respect to stationary block 15, can be controlled so that rod 10 is tilted to compensate for tilt of sample 11. Flexible bellows 22 is disposed between micrometer head 13 and stationary block 15 so as to surround sample rod 10. Cover 24 is located above sleeve 18 with O-ring 23 between them, surrounding rod 10 which projects from the sleeve.

A plurality of stays 25, e.g., four in number, protrude vertically from the lower surface of base plate 3 so that their respective lower portions can be immersed in liquid nitrogen 6 in adiabatic vessel 4. Nonmagnetic support base 26 of supporting means 60 is fixed to the respective lower end portions of stays 25 so as to extend horizontally. Acoustic lens 27 is supported on base 26 for displacement in the x- and y-directions by means of an elastic support mechanism. Electromagnetic drive mechanism is provided to drive lens 27 in the x-and y-directions. Stays 25 are formed of a material whose coefficient of thermal expansion is substantially equal to that of sample rod 10.

Figure 2:
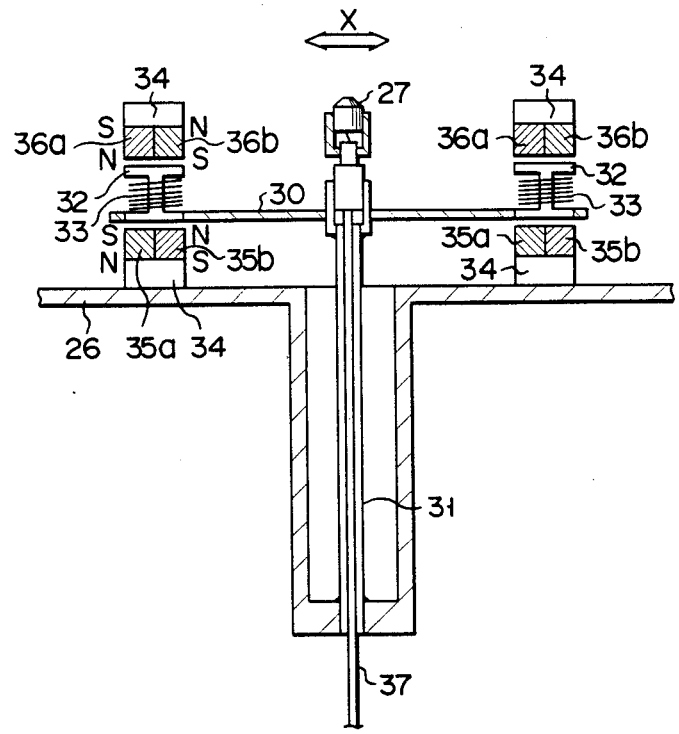
FIG. 2 is an enlarged view of an acoustic lens shown in FIG. 1.

FIG. 2 shows arrangements of the elastic support mechanism and the electromagnetic drive mechanism for acoustic lens 27. Lens 27, which is formed of a nonmagnetic material, is supported on the center of cross-shaped movable member 30 formed of four arm portions intersecting one another at right angles. Member 30 is supported on support base 26 for displacement in the x- and y-directions by means of hollow flexible pillar 31. The top portion of pillar 31 is connected to the center of member 30. Flexible pillar 31, which is formed of, e.g., a stainless-steel tube, is capable of elastic deformation. Each arm portion of movable member 30 is provided with coil 33, which includes bobbin 32, formed of a nonmagnetic material such as aluminum, and covered copper wire wound thereon. Thus, two pairs of coils 33 (only one pair for the x-direction is shown in FIG. 2) are arranged individually at symmetrical positions in the x- and y-direction, with respect to acoustic lens 27. Square or U-shaped yokes 34 are disposed on support base 26, corresponding individually to coils 33. Two pairs of permanent magnets 35a, 35b and 36a, 36b are fixed to each yoke 34 so as to face one another across coil 33. In this arrangement, magnetic fluxes of opposite directions pas at the opposite side portions with respect to the driving direction.

Thus, in the present embodiment, when a required current is applied to one of coils 33 in each pair, it is combined with the magnetic fluxes of permanent magnets 35a, 35b, 36a and 36b to make an electromagnetic action. This action causes movable member 30 to drive acoustic lens 27 two-dimensionally in the x- and y-directions. In this manner, sample 11 is twodimensionally scanned with an ultrasonic beam emitted from lens 27, and the region for the scanning, i.e., the field of view, is selected. When the other of coils 33 in each pair is moved, a current is caused to flow through it by an electromotive force. By detecting this current, therefore, the moving speed of acoustic lens 27 may be monitored. Coaxial cable 37, which is connected to lens 27, is passed through flexible pillar 31, led to the outside through the side wall portion of adiabatic vessel 4, or opening 3a of base plate 3, and a sealing device, and connected to a signal processing circuit. The lead wire of each coil 3 is also led to the outside through the sealing device, and connected to a driver circuit.

FIGS. 3A and 3B show arrangements of an x-axis driver circuit and a y-axis driver circuit for driving acoustic lens 27 in the x- and y-directions, respectively. The x-axis driver circuit shown in FIG. 3A is arranged so that the output of sine-wave generator 40 is supplied to one input end of adder 42 through attenuator 41 for adjusting the amplitude of the output of generator 40, required voltage Vx from variable voltage source 43 is applied to the other input end of adder 42, and the output of adder 41 is supplied to x-axis drive coil 33 through power amplifier 44. The y-axis driver circuit shown in FIG. 3B is arranged so that the output of sawtooth-wave generator 45 is supplied to one input end of adder 47 through attenuator 46, required voltage Vy from variable voltage source 48 is applied to the other input end of adder 47, and the output of adder 47 is supplied to y-axis drive coil 33 through power amplifier 49. The respective outputs of generators 40 and 45 are synchronized so that acoustic lens 27 can be two-dimensionally scanned in the x- and y-directions.

According to this arrangement, acoustic lens 27 is moved for a distance corresponding to output voltage Vx of variable voltage source 43, in the x-direction, by means of flexible pillar 31, and undergoes sine oscillation around the reached position in response to a sine-wave signal. In the y-direction, lens 27 is moved for a distance corresponding to output voltage Vy of variable voltage source 48 by means of pillar 31, and undergoes a y-direction displacement compared to the reached position. Thus, sample 11 is two-dimensionally scanned in the x- and y-directions, within ranges corresponding to the outputs of attenuators 41 and 46, starting at positions corresponding to voltages Vx and Vy. Accordingly, the field of view can be automatically selected as required by adjusting output voltages Vx and Vy of voltage sources 43 and 48. Moreover, the displacement of acoustic lens 27, observed during this field selection, is attributable only to the elastic deformation of flexible pillar 31 which supports the lens. Therefore, the field of view can be selected with high accuracy and reproducibility. Since the field of view can be selected electrically, furthermore, the operating efficiency is high enough to permit computer control with ease.

FIG. 4 shows a modification of the driver circuit arrangement. In this modification, the x- and y-axis driver circuits shown in FIGS. 3A and 3B are arranged so that the output of sine-wave generator 40 is supplied alternatively to attenuators 41 and 46, and the output of sawtooth generator 45 is supplied alternatively to attenuator 46. Thus, x- and y-axis tilt correction modes can be selected as well as the aforementioned xy scanning mode. In the tilt correction modes, acoustic lens 27 is oscillated alternatively in the x- and y-directions by means of the output of generator 40, thereby correcting the tilt of sample 11 in each direction. To attain this, three-contact switches 51 and 52 are disposed between sine-wave generator 40 and attenuator 4 and between sawtooth generator 45 and attenuator 46, respectively. In this arrangement, the output of attenuator 41 is supplied to first and third contacts A1 and A3 of switch 51 and second contact B2 of switch 52, while the output of attenuator 45 is supplied to third contact B3 of switch 52. Movable contacts A4 and B4 of switches 51 and 52, which are connected to attenuators 41 and 46, respectively, are shifted in association with each other. Thus, if first contacts A1 and B1 of switches 51 and 52 are selected by means of movable contacts A4 and B4, respectively, the x-axis tilt correction mode is established. If second contacts A2 and B2 are selected, the y-axis tilt correction mode is established, and if third contacts A3 and B3 are selected, the xy scanning mode is established. The scanning position on sample 11, in the x- and y-axis tilt correction modes, can be adjusted by means of variable voltage sources 43 and 48, respectively. The field selection in the xy scanning mode can be regulated by means of voltage sources 43 and 48, as mentioned before.

The following is a description of operation modes of the x- and y-axis driver circuits shown in FIG. 4.

Figure 5:
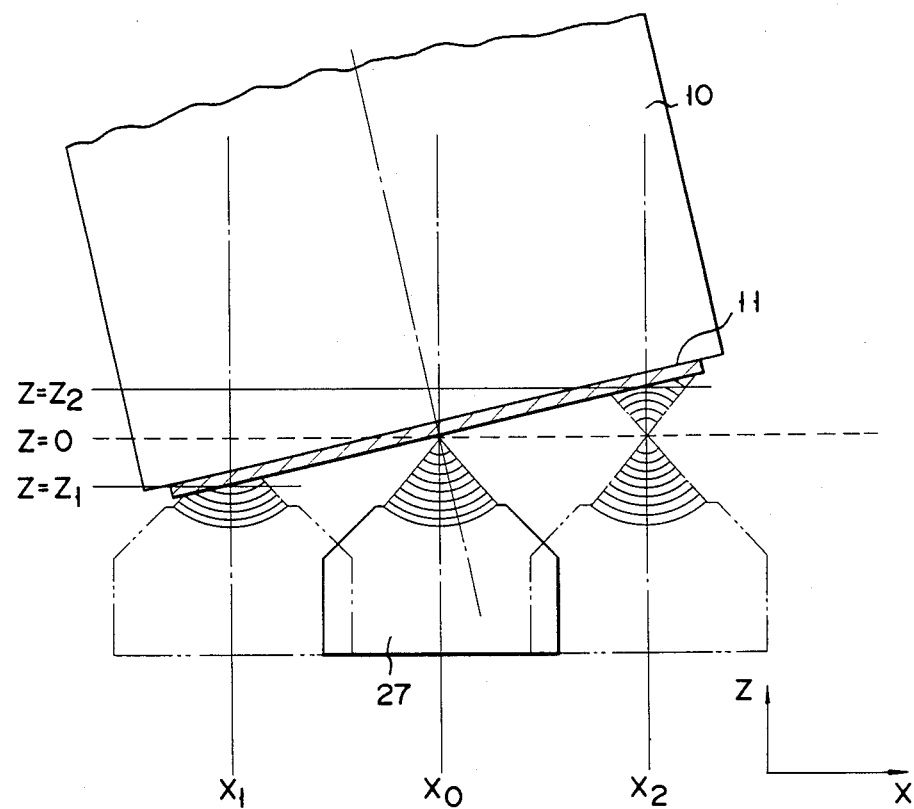
FIGS. 5, 6 and 7 are diagrams for individually illustrating operation modes.

FIG. 5 shows relative positions of acoustic lens 27 and sample 11 taken when the surface of the sample is tilted with respect to the focal plane of of the lens. Here let it be supposed that the x-direction scanning range of acoustic lens 27 is $x=x_1$ to $x=x_2$, and the focus of lens 27 is situated on the sample surface when intermediate position $x=x_0$ is reached. Let us suppose also that the height of the sample surface is on the level of z-direction origin $z=0$ (so that the focal plane of lens 27 is parallel to the xy plane given by $z=0$), and the heights of the sample surface corresponding to $x=x_1$ and $x=x_2$ are given by $z=z_1$ and $z=z_2$, respectively.

Figure 6:
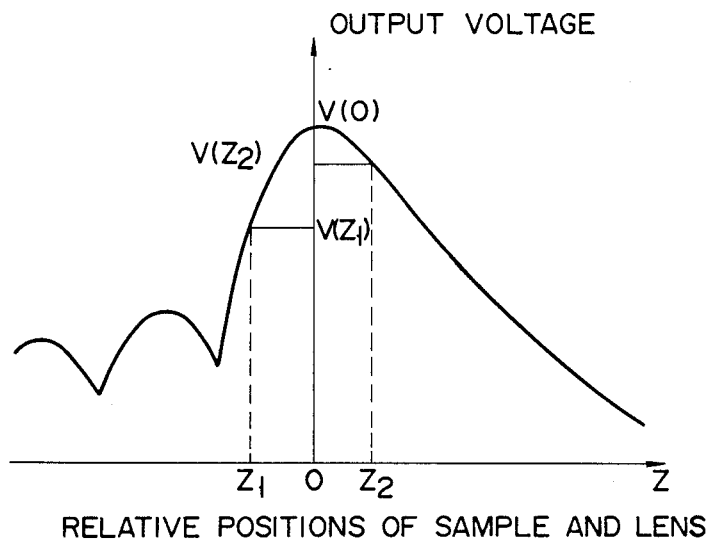

If the distance between the sample and the acoustic lens is changed at any desired point on the sample, a so-called $V_{(z)}$-curve, which depends on the material of the sample, can be obtained, as shown in FIG. 6. In FIG. 6, the axis of abscissa represents the relative positions of the sample and the acoustic lens. Point $z=0$ indicates the position where the focus of the lens is situated on the sample surface, the positive direction is the direction in which the sample and the lens move away from each other, and the negative position is the direction in which the sample and the lens approach each other. The axis of ordinate represents effective value V, for example, of the output voltage of ultrasonic waves reflected by the sample, which has a maximum at $z=0$. Thus, outputs corresponding to positions $x=x_1$, $x=x_0$, and $x=x_2$ of acoustic lens 27, in FIG. 5, are given by $V_{(z1)}$, $V_{(0)}$, and $V_{(z2)}$, respectively, in FIG. 6.

Figure 7:
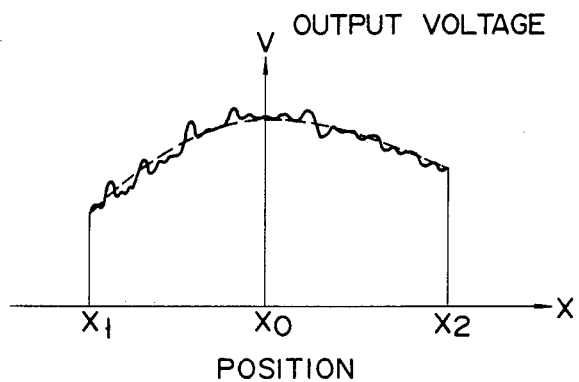

FIG. 7 shows a display of the output voltage obtained by scanning acoustic lens 27 in the x-direction, for sample 11 tilted as shown in FIG. 5. Within the range of $x_1 \leq = x \leq = x_0$, distance z between the focal plane of lens 27 and the sample surface is reduced from $z = z1$ to $z=0$. As seen from FIG. 6, therefore, the output voltage increases from $V(z1)$ to $V(0)$. Actually, it increases in a fluctuating curve, as indicated by the full line, based on the broken line of FIG. 7. Within the range of $x_0 \leq = x \leq = x_2$, on the other hand, the output voltage decreases along the broken base line.

Thus, if acoustic lens 27 is scanned in one direction within the xy scanning plane when the sample surface is tilted with respect to the focal plane of the lens, the base line of the output voltage inclines corresponding to the tilt of the sample surface.

In this modification, therefore, the first contacts of switches 51 and 52 are selected to establish the x-axis tilt correction mode, for example. While monitoring the output voltage for this case, x-direction adjust screws 20 and 21 shown in FIG. 1 are adjusted so that the base line of the output voltage is constant, thereby tilting sample rod 10 in the x-direction to correct the x-direction tilt of sample 11. Thereafter, the second contacts of switches 51 and 52 are selected to establish the y-axis tilt correction mode. While monitoring the output voltage for this case, the y-direction adjust screws are adjusted so that the base line of the output voltage is constant, thereby tilting sample rod 10 in the y-direction to correct the y-direction tilt of sample 11. The output frequency of sine-wave generator 40 for these tilt correction modes must only be about 20 Hz, so that the base line obtained with tilted rod 10 can be monitored at real time.

After the tilt of sample 11 in the x- and y-directions is corrected in this manner, the third contacts of switches 51 and 52 are selected to establish the xy scanning mode. By doing this, an ultrasonic image of a desired region of sample 11 can be obtained.

Thus, with use of the driver circuits shown in FIG. 4, the tilt of the sample surface can be corrected at real time while observing information indicative of the tilt, i.e., the base line of the output voltage curve. In contrast with the conventional case in which the tilt of sample 11 is corrected after observing an ultrasonic image obtained by xy-scanning the sample, therefore, the tilt correction can be achieved more accurately and speedily.

Figure 8:
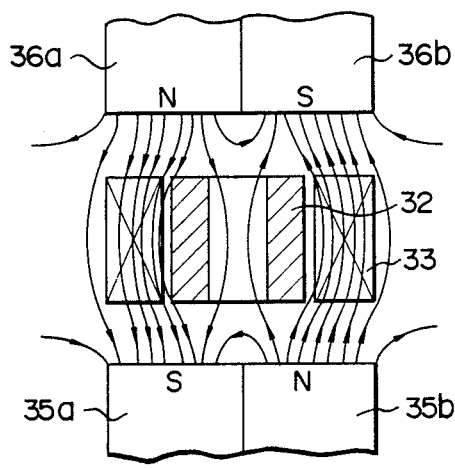
FIG. 8 shows a modification of the present invention.

It is to be understood that the present invention is not limited to the embodiment described above, and that various changes and modifications may be effected therein by one skilled in the art without departing from the scope or spirit of the invention. In the embodiment described above, for example, coils 33 are formed of covered copper wire. Alternatively, however, they may be formed of covered iron wire. In this case, coils 33 are increased in permeability, and the magnetic flux density at the coil portions is higher, so that the driving efficiency is improved. Moreover, the material of bobbins 32 is not limited to aluminum or other nonmagnetic material. Alternatively, the bobbins may be formed of superconducting metal (e.g., niobium alloy) which has high transition temperature and high critical magnetic field. In this case, bobbins 32 are disposed, in liquid helium. According to this arrangement as shown in FIG. 8, the magnetic fluxes, which naturally should penetrate bobbins 32, are forced out by the Meissner effect of the superconductor. As a result, the magnetic flux density in the vicinity of coils 33 becomes higher, so that the driving efficiency is further improved. In the embodiment described above, moreover, the acoustic lens 27 is driven by means of paired coils 33 in the x- and y-directions. Alternatively, however, the pair of coils may be composed of a driving coil and a detecting coil, which are arranged so that the output of the detecting coil is subjected to motional feedback to the driving coil, whereby the drive of the detecting coil is controlled. With this arrangement, the xy scanning and field selection can be performed with higher accuracy. In the above embodiment, furthermore, acoustic lens 27 is driven in the x- and y-directions. Alternatively, however, sample rod 10 may be driven in the x- and y-directions, or rod 10 and lens 27 may be driven in the x- and y-directions or in the y- and x-directions, respectively. Further, the present invention is not limited to the cryogenic ultrasonic microscope described above, and may also be effectively applied to conventional normal-temperature ultrasonic microscopes which use water or the like as the ultrasonic transmission medium.

According to the present invention, as described herein, an acoustic lens and sample supporting means are relatively two-dimensionally driven by means of electromagnetic drive means, thereby permitting control of a scanning region or view field selection, as well as scanning for the formation of an ultrasonic image of a sample. Thus, with use of a simple arrangement, a desired field of view can be automatically selected with high accuracy and reproducibility.

What is claimed is:

1. An ultrasonic microscope comprising:
an acoustic lens;
accoustic lens supporting means;
sample supporting means for supporting a sample to face the acoustic lens; and
drive means for two-dimensionally shifting the acoustic lens supporting means and the sample supporting means relative to each other, thereby setting a scanning region, and for causing the sample to be scanned to obtain an ultrasonic image thereof;
wherein said drive means includes first shift means for shifting the acoustic lens supporting means in a first direction by means of magnetic force, and second shift means for shifting the acoustic lens supporting means in a second direction, perpendicular to the first direction, by means of magnetic force;
wherein said first and second shift means each include a magnetic field generating coil fixed to the acoustic lens supporting means, a power circuit for supplying an electric current to the coil, and magnetic means for generating magnetic fields which, in conjunction with a magnetic field generated when an electric current flows through the coil, cause the coil to shift in the first and second directions, individually;
wherein said power circuit includes a first power source means for providing an electric signal for displacing the acoustic lens supporting means to a designated position within said scanning region, a second power source means for providing an electric signal to produce scanning of said sample about said designated position, an adder for adding the electric signals from the first and second power source means, and means for delivering the resulting signal to the coil to cause said drive means to displace the acoustic lens supporting means to said designated position and to produce scanning.

2. The ultrasonic microscope according to claim 1, wherein said first and second power source means include a variable voltage source and a waveform signal current source, respectively.

3. An ultrasonic microscope comprising:

an acoustic lens;
a sample;
supporting means for supporting the acoustic leans and the sample for two-dimensional movement relative to each other so that the lens and the sample face each other; and
drive means for two-dimensionally shifting the acoustic lens and the sample relative to each other, thereby setting a scanning region, and driving the supporting means to scan the sample to obtain an ultrasonic image thereof, said drive means including magnetic means for shifting the supporting means by generating a magnetic field, a first power source means for providing an electric signal to designate a position in the scanning region, a second power source means for providing an electric signal to produce scanning about said position, and an adder for adding the electric signals from the first and second power source means and delivering the resulting signal to the magnetic means to cause said drive means to shift the supporting means to said designated position and to scan the sample about said designated position.

4. The ultrasonic microscope according to claim 3, which includes elastic means for elastically restoring the supporting means to the original position thereof when the supply of the resulting signal to the magnetic means is stopped.

5. The ultrasonic microscope according to claim 3, wherein said first power source mans is capable of driving the acoustic lens supporting means at a speed greater than said second power source means.

6. The ultrasonic microscope according to claim 1, wherein said electric signal from the first power source means displaces the acoustic lens supporting means to said designated position before the second power source means produces said scanning.

7. The ultrasonic microscope according to claim 1, wherein said first power source means is capable of driving the acoustic lens supporting means at a speed greater than said second power source means.

8. An ultrasonic microscope, comprising:
an acoustic lens;
acoustic lens supporting means;
means for supporting a sample;
first and second magnetic means perpendicular to each other and moving the sample and lens relative to each other in a two-dimensional direction by means of magnetic force;
first driving means for driving the second magnetic means at a high speed;
second driving means for driving the second magnetic means at a speed lower than said high speed;
switching means for selectively connecting the first driving means to one of the first and second magnetic means;
monitoring means for displaying in real time on an abscissa axis a shifting value of the direction in which the sample and lens are relatively moved by the first driving means, and an output signal from the lens on an ordinate axis; and
means for correcting a tilt between the sample and lens in said two-dimensional direction based on said shifting value.

* * * * *